United States Patent
Falck et al.

(10) Patent No.: US 7,859,401 B2
(45) Date of Patent: Dec. 28, 2010

(54) ADDRESSING SCHEME FOR SMART WIRELESS MEDICAL SENSOR NETWORKS

(75) Inventors: Thomas Falck, Aachen (DE); Pedro Masegosa De Miguel, Barcelona (ES)

(73) Assignee: Koninklijke Philips Electronics N.V., Eindhoven (NL)

( * ) Notice: Subject to any disclaimer, the term of this patent is extended or adjusted under 35 U.S.C. 154(b) by 666 days.

(21) Appl. No.: 11/908,533

(22) PCT Filed: Mar. 13, 2006

(86) PCT No.: PCT/IB2006/050781
§ 371 (c)(1),
(2), (4) Date: Sep. 13, 2007

(87) PCT Pub. No.: WO2006/100620
PCT Pub. Date: Sep. 28, 2006

(65) Prior Publication Data
US 2008/0191866 A1    Aug. 14, 2008

Related U.S. Application Data

(60) Provisional application No. 60/664,103, filed on Mar. 22, 2005.

(51) Int. Cl.
G08B 1/08 (2006.01)
G08B 9/00 (2006.01)
H02J 13/00 (2006.01)
H04L 9/32 (2006.01)
G06F 15/173 (2006.01)

(52) U.S. Cl. ............ 340/539.12; 340/286.02; 340/573.1; 340/825.52; 713/168; 713/170; 713/171; 709/224

(58) Field of Classification Search ............ None
See application file for complete search history.

(56) References Cited

U.S. PATENT DOCUMENTS

| | | |
|---|---|---|
| 6,832,251 B1 | 12/2004 | Gelvin et al. |
| 2002/0109621 A1 | 8/2002 | Khair et al. |
| 2004/0078219 A1 | 4/2004 | Kaylor et al. |
| 2004/0107366 A1 | 6/2004 | Balfanz et al. |
| 2006/0122469 A1* | 6/2006 | Martel .................. 600/300 |
| 2009/0174547 A1* | 7/2009 | Greene et al. ........ 340/539.13 |

FOREIGN PATENT DOCUMENTS

DE    10255349 A1    11/2003

OTHER PUBLICATIONS

Gay, D., et al.; The nesC Language: A Holistic Approach to Networked Embedded Systems; 2003 http://www.nescc.sourceforge.net.

(Continued)

*Primary Examiner*—Julie Lieu

(57) ABSTRACT

A wireless body network (8) for monitoring a patient (16, 32), the wireless body network (8) includes at least one wireless unit (10, 12, 14, 34, 36, 38, 40) coupled to the patient (16, 32) configured to collect and transmit data to the wireless body network related to one physiological function of the patient. The wireless unit (10, 12, 14, 34, 36, 38, 40) employs an addressing scheme (80), including a patient identification field (82) that contains a patient identification number that is unique to the wireless body network; at least one of a service type field (84) that contains a service type and a point type field (86) that indicates whether the wireless unit (10, 12, 14, 34, 36, 38, 40) provides a service or consumes a service; and a point identification field (88) that distinguishes one wireless unit (10, 12, 14, 34, 36, 38, 40) from another when the patient identification field (82), the service type field (84) and the point type field (88) are identical. A physical device (22, 24, 26, 28) is configured to communicate with the wireless unit (10, 12, 14, 34, 36, 38, 40) utilizing the addressing scheme (80).

21 Claims, 5 Drawing Sheets

OTHER PUBLICATIONS

Jeong, J., et al.; Incremental Network Programming for Wireless Sensors; 2004.

Lamprinos, I. E., et al.; A Low Power Medium Access Control Protocol for Wireless Medical Sensor Networks; 2004; Proc. 26th Annual Intl. Conf. IEEE; pp. 2129-2132.

Levis, P., et al.; The Emergence of Networking Abstractions and Techniques in TinyOS; 2004 http://www.tinyos.net/media/html.

Welsh, M., et al.; Wireless Sensor Networks for Emergency Medical Care; 2004 www.eecs.harvard.edu/.

* cited by examiner

US 7,859,401 B2

ADDRESSING SCHEME FOR SMART WIRELESS MEDICAL SENSOR NETWORKS

CROSS REFERENCE TO RELATED APPLICATIONS

This application claims the benefit of U.S. provisional application Ser. No. 60/664,103 filed Mar. 22, 2005, which is incorporated herein by reference.

The following relates to wireless body networks. It finds particular application with addressing schemes associated with smart wireless medical sensor networks for patient monitoring applications and treatment controlling applications, and will be described with particular reference thereto. However, it is to be appreciated that the invention may also find application in providing addressing schemes to wireless sensors associated with monitoring a multiplicity of real time events such as location tracking, medication dosing and the like.

Patients typically require monitoring of one or more physiological functions when they receive medical attention. For example, it may be desirable to monitor heart function, pulse, blood pressure, blood oxygen level and the like. Conventionally, such monitoring is accomplished utilizing sensors wired to various output devices that can notify medical personnel of one or more conditions. Alternatively, wireless sensors can be employed with wireless networks to transmit such data to one or more receiving elements such as a display, a monitor, memory, central terminal and the like.

Typically, wireless sensors have a unique address, hard coded address, e.g. a fixed number. Although these addresses are unique, there is no particular meaning associated with such addresses. Instead, the addresses simply provide a unique identifier to facilitate communication from one party to another, when sending information through a network.

Today's devices have IP addresses that are based on network topology and are not related to device capabilities. To find a device offering a particular service, an application must employ name resolution protocols such as domain name servers (DNS), for example. In this manner, the DNS can map meaningful high-level names to IP addresses or service directory protocols such as universal plug and play (UPnP). However, such protocols are not suited for resource constrained wireless sensor networks.

The present invention contemplates an improved apparatus and method that overcomes the aforementioned limitations and others.

According to one aspect, a wireless body network (8) for monitoring a patient (16, 32), the wireless body network (8) includes at least one wireless unit (10, 12, 14, 34, 36, 38, 40) coupled to the patient (16, 32) configured to collect and transmit data to the wireless body network related to one physiological function of the patient. The wireless unit (10, 12, 34, 36, 38, 40) employs an addressing scheme (80), including a patient identification field (82) that contains a patient identification number that is unique to the wireless body network; at least one of a service type field (84) that contains a service type and a point type field (86) that indicates whether the wireless unit (10, 12, 14, 34, 36, 38, 40) provides a service or consumes a service; and a point identification field (88) that distinguishes one wireless unit (10, 12, 14, 34, 36, 38, 40) from another when the patient identification field (82), the service type field (84) and the point type field (88) are identical. A physical device (22, 24, 26, 28) is configured to communicate with the wireless unit (10, 12, 14, 34, 36, 38, 40) utilizing the addressing scheme (80).

According to another aspect, a method for communicating within a wireless medical sensor network (8) includes a plurality of wireless units (10, 12, 14, 34, 36, 38, 40), comprising broadcasting to at least one of the wireless units (10, 12, 14, 34, 36, 38, 40) employing an addressing scheme. The addressing scheme includes a patient identification field (82) that contains a patient identification number that is unique to the wireless body network (8); at least one of a service type field (84) that contains the service type value and a point type field (86) that contains the point value indicative of whether the wireless unit (10, 12, 14, 34, 36, 38, 40) provides a service or consumes a service; and a point identification field (88) that contains the point identification value to distinguish one wireless unit (10, 12, 14, 34, 36, 38, 40) from a disparate wireless unit (10, 12, 14, 34, 36, 38, 40) when the patient identification field (82), the service type field (84) and the point type field (86) are identical.

One advantage of the present invention is that it facilitates transmission of information related to physical devices across a smart wireless medical sensor network.

Another advantage of the present invention is that addressing of physical devices in the network can be autonomously addressed.

Another advantage is that the addressing scheme related to the physical devices is based on functionality of the device and not location within the network. Numerous additional advantages and benefits will become apparent to those of ordinary skill in the art upon reading the following detailed description of the preferred embodiments.

The invention may take form in various components and arrangements of components, and in various steps and arrangements of steps. The drawings are only for purposes of illustrating the preferred embodiments and are not to be construed as limiting the invention.

Figure 1:
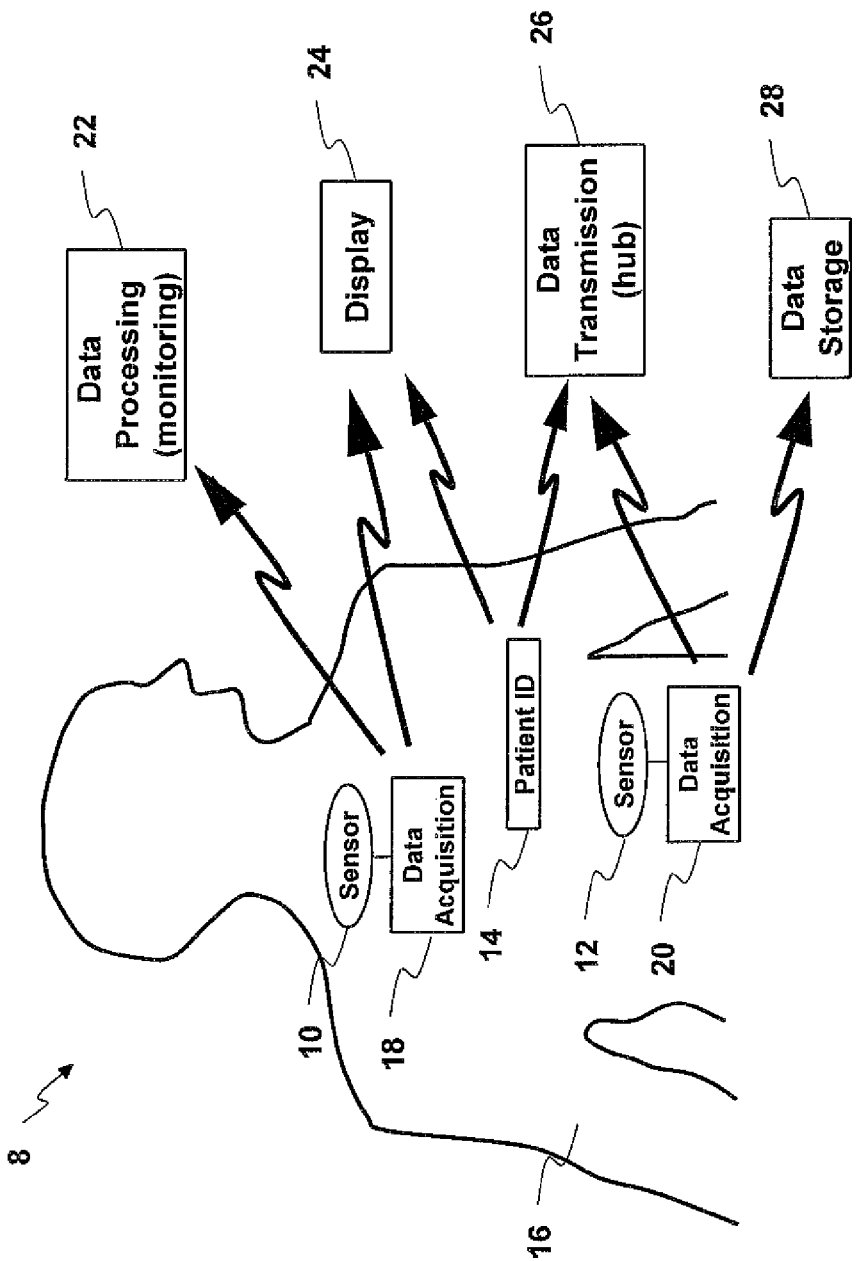
FIG. 1 illustrates a wireless body network with wireless sensors communicating with various physical devices.

A wireless body network 8 for patient monitoring is shown that includes a plurality of nodes, such as a first wireless sensor 10, a second wireless sensor 12, and a patient ID module 14. The nodes transmit information related to various aspects of a patient 16. As used herein, "sensor" also can connote a controlled device, such as a medication dosing unit, a drip feeder control, an electrotherapy device, and the like. The patient ID module 14 transmits a signal unique to the patient 16 for patient identification purposes. The wireless sensors 10, 12 are coupled to data acquisition components 18 and 20, respectively. Each data acquisition component 18, 20 acquires data related to the physiological function of a patient monitored by the corresponding wireless sensor 10, 12 and transmits the information to one or consuming devices. Typical consuming devices include a data processing component 22, a display device 24, a data transmission component 26, and a data storage component 28. Nodes directly communicate with each other via a wireless body network 8. Rather than routing of packets, the wireless body network 8 is preferably a one hop peer-to-peer network over which devices within a range of five to ten meters can communicate. Other routing schemes are also contemplated. For example, the data acquisition units of each sensor associated communicate with the patient ID node which channels the data from that patient to a local off-patient transmission hub for further distribution.

The wireless sensors 10, 12 can acquire patient data utilizing an electrocardiograph (ECG) sensor, a pulse oximetry (SpO$_2$) sensor, a non-invasive blood pressure (NIBP) sensor, a temperature sensor and the like. The wireless sensors 10, 12, the patient ID module 14, the data processing component 22, the display device 24, the data transmission component 26, and the data storage component 28 are all points that provide and/or consume data. Points that provide data are service points and points that consume data are control points. A service point provides one service and a control point consumes one service. A node can host any combination of service and control points. As illustrated, the wireless sensors 10, 12 and patient ID module 14 are service points since they provide data to the wireless ad hoc network. In contrast, the data processing component 22, the display device 24, the data transmission component 26, the data storage component 28, medication dosing devices, and the like consume data are control points. Each point is autonomously assigned a network-wide unique address composed of patient ID, service type, point type, and point ID.

The sensors 10, 12 that communicate with the nodes in the wireless body network 8 are autonomously addressed. No central entity is required to assign addresses. The service type and point type is typically built into each sensor and is known prior to connection to the network. Each patient has their own ID node 14 that transmits a unique patient ID. When a patient has only one type of sensor on his or her body (e.g., SpO$_2$, temperature, ECG, NIBP, etc.), conflicts between different sensor types are mitigated. However, conflicts may arise when the patient has a plurality of sensors of the same service type and point or a plurality of different sensors.

The node addresses are independent of network topology and are based instead on capabilities that are relevant to applications. The present addressing scheme provides the basis for simple and efficient automatic assignment of network addresses, service discovery and eventing protocols. Lightweight protocols are important for wireless sensors, since they are resource-constrained with regard to bandwidth, memory, processor, and power.

The data processing component 22 manipulates received data. In one example, the data processing component is programmed to trigger an alarm when particular data falls outside of predetermined thresholds. In another example, the processing component averages a plurality of received measurements, logs data to memory, provides statistical analyses, and derives time dependent metrics and so on.

The display device 24 receives wireless signals and presents data in a variety of formats. In one approach, bar graphs, pie charts, logarithmic graphs, and the like are employed to present data. In another approach, the data is presented in an audio format such as voice emulation, alarm signals and the like. In another approach, the display presents data in one or more remote locations (e.g., via a wireless network, LAN, WAN, etc.) Additionally, a user interface (not shown) can be employed to change the type and manner in which data is presented.

The data transmission component 26 routes data from the patient 16 to substantially any disparate receiving component. For example, data can be routed to a remote display device, remote data storage, and the like. Also, the data transmission component can allow a plurality of components to access data at substantially the same time.

The data storage component 28 stores data for access by one or more components. Stored data is organized and indexed to facilitate retrieval by one or more applications that have specific data organization and/or formatting requirements. Additionally, data storage is optimized so as to store data on a periodic basis, when a particular condition is met, and the like.

As noted, some nodes (e.g., an ECG sensor) provide data; some consume data (e.g., a display); and some nodes both consume and provide data (e.g., a monitoring unit). Services can be distinguished by data source (e.g., sensor, storing unit, processing unit, patient identifier, etc.) and data type (e.g., ECG, SpO$_2$, temperature, NIBP, patient data, etc.). This leads to the identification of different service types as shown, for example, in Table 1 below:

TABLE 1

| Data Sources | Data Types | | | | |
|---|---|---|---|---|---|
| | ECG | SpO$_2$ | Temperature | NIBP | Patient data |
| Sensor | ECG Sensor data | SpO$_2$ Sensor data | Temperature Sensor data | NIBP Sensor data | |
| Storing Unit | ECG Stored data | SpO$_2$ Stored data | Temperature Stored data | NIBP Stored data | |
| Processing Unit | ECG Processed data | SpO$_2$ Processed data | Temperature Processed data | NIBP Processed data | |
| Hub | ECG Hub data | SpO$_2$ Hub data | Temperature Hub data | NIBP Hub data | |
| Patient ID | | | | | Patient data |

Figure 2:
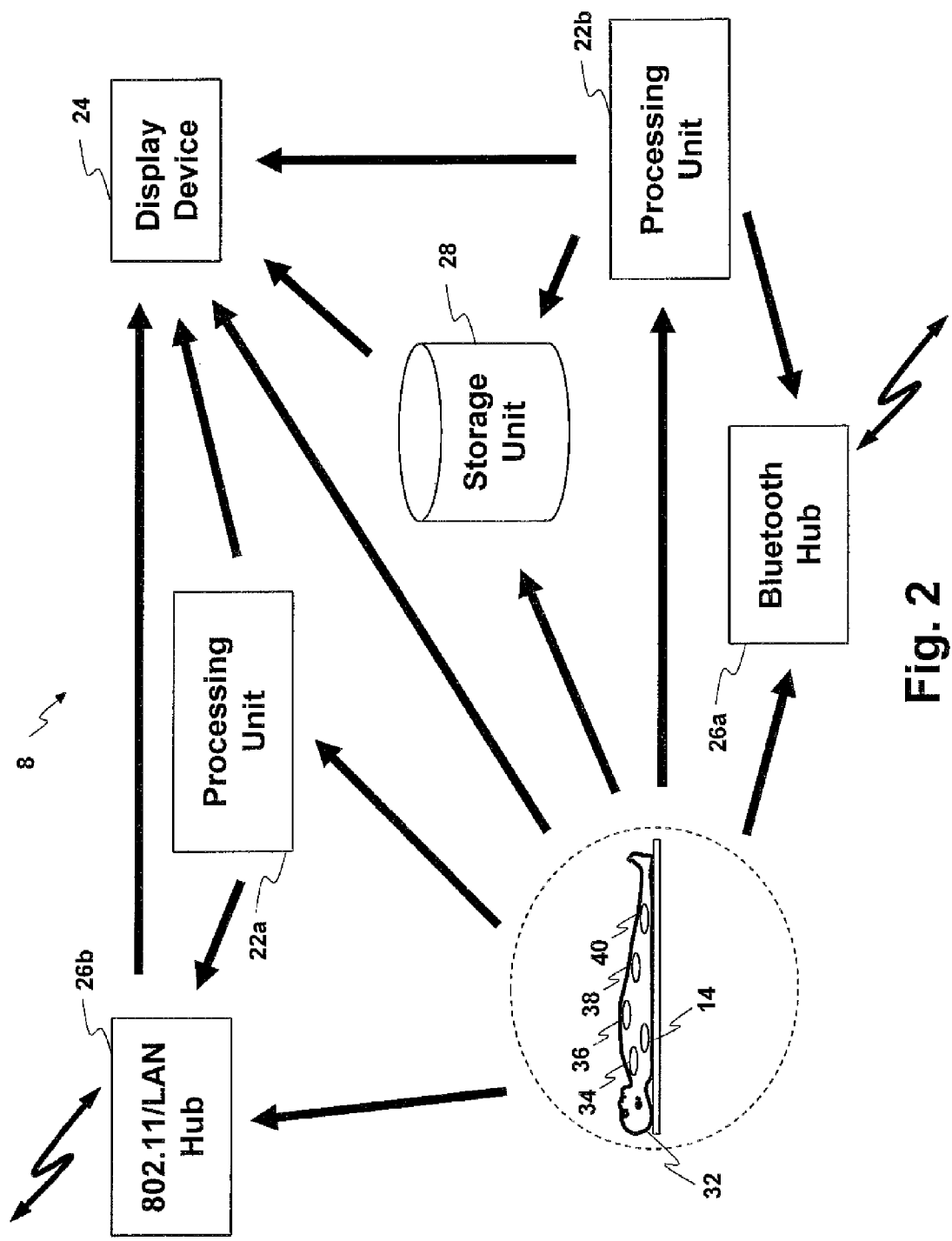
FIG. 2 illustrates a wireless network in which information is transmitted from service points associated with a patient to a plurality of control points.

FIG. 2 shows another example of the wireless sensor network 8 containing the above-referenced service types. Each arrow in the picture depicts the interest of service consumers in the services offered by service providers. The patient 32 is coupled to service points including an ECG sensor 34, a SpO$_2$ sensor 36, a NIBP sensor 38, a temperature sensor 40 and the patient identifier module 14. The service points broadcast information to a plurality of devices within the wireless sensor network 8. Several physical devices nodes receive and/or transmit data received from the service points. A first processing unit 22a, a second processing unit 22b and the storage unit 28 accept and process and/or store data received from the service points. Data is transmitted outside the wireless sensor network via a Bluetooth hub 26a and/or an 802.11b/LAN hub 26b utilizing wireless protocols well known in the art. The display device 24 receives data from the physical devices for presentation and/or transmission to one or more other control points.

Figure 3:
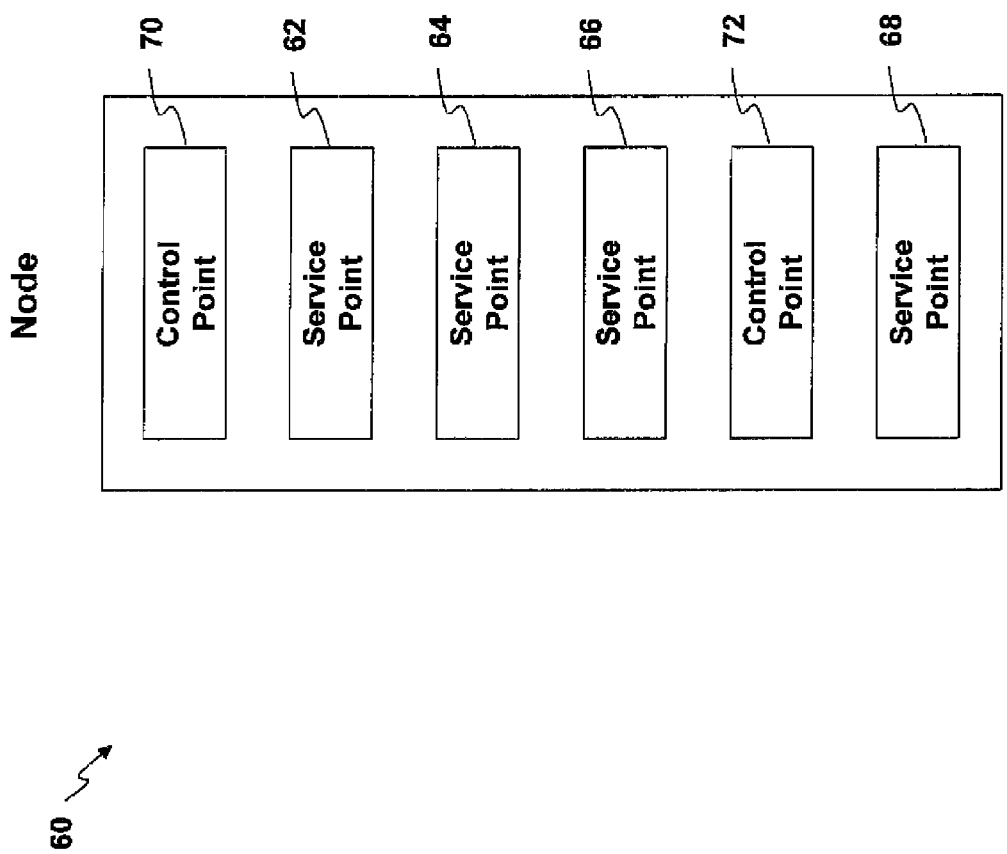
FIG. 3 illustrates a node that contains several service points and control points in accordance with the present invention.

As illustrated in FIG. 3, a node 60 located within a wireless network can contain one or more service points 62, 64, 66, 68 and/or control points 70, 72. In one example, the node 60 is a monitoring unit and each point has a network-wide unique address. Addressing is based on the properties of a point and not on network topology. In one approach, a physical device and each associated node host combinations of control points and/or service points.

One physical device can utilize more than one address. If two or more addresses are employed with one physical device, the physical device is shared and receives all packets sent throughout a wireless ad hoc network. The physical device determines if the packet address matches the physical device and if so, processes the information contained in the packet. In one example, a physical device is a control point to receive data sent from a temperature sensor with a particular point ID.

Figure 4:
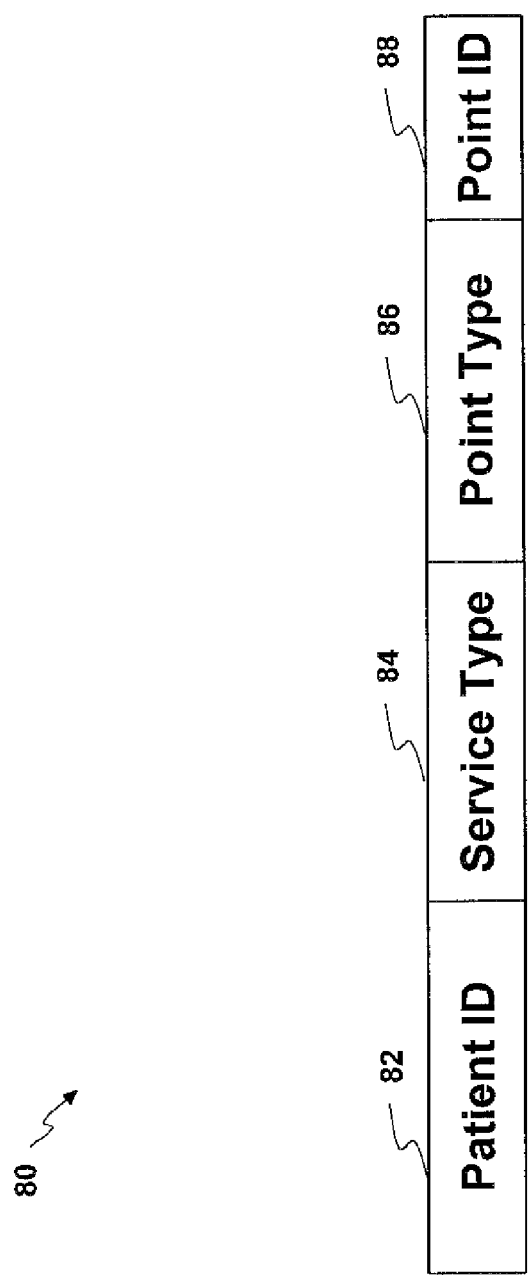
FIG. 4 shows an addressing schema employed with either a service point or control point to provide information relating to the functionality of the device instead of location within a network topology.
Figure 5:
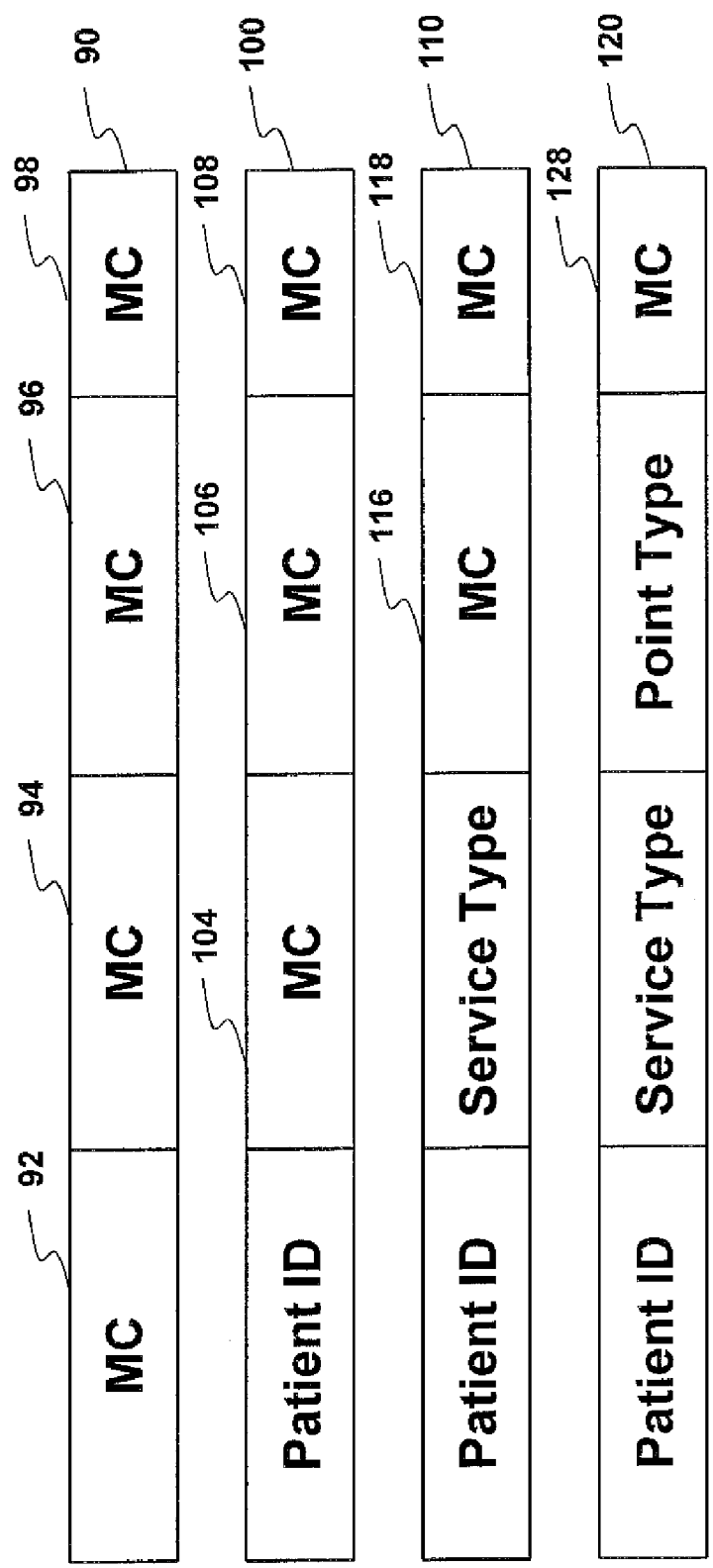
FIG. 5 shows an addressing schema that allows multicasting to predetermined fields within the address.

FIG. 4 illustrates a point address 80 that includes four fields 82, 84, 86, 88 related to the device type, functionality, and associated patient from which the data is delivered. The point address 80 is employed by one or more service points and/or control points. A patient identification field 82 contains the hospital wide unique patient identifier number. A service type field 84 contains the service type. As noted, typical service types include ECG, NIBP, SpO₂, temperature, and the like. A point type field 86 indicates whether the point is a service point or a control point. A point identification field 88 enables points that have the same patient identification, service type and pointing type to be distinguished from one another. In addition, the point address allows sending or multi-casting to a group of points. Each field reserves one value for multicast addressing as shown in FIG. 5.

The service type field 84 and point type field 86 have fixed values that are inherent based on the associated physical device. For example, if an ECG sensor provides data to one or more control points in a wireless network, then the service type is "ECG" and the point type is "service." In contrast, the patient ID field 82 and the point ID field 88 are dynamic and are assigned in one of a plurality of ways. In one approach, for assigning the patient ID is the patient ID module 14 queries all other patient ID modules in the network to ascertain a unique patient ID. Alternatively, the patient ID can be the same as the ID which the hospital assigned the patient.

It is to be appreciated that the sequence of the fields 82-88 can be in any order. When a packet is received, all fields 82-88 are read to gather the information transmitted from a particular service point and/or consumed by a control point. Additional fields (not shown) can be added to the point address to transmit various pieces of information such as building a hierarchy of networks, for example. In one example, the additional fields relate to the location of the wireless sensors such as a floor, a medical center, a ward and so on.

In another approach, the point type field and the service type filed are combined. Different point IDs are employed with a particular sensor. In addition, the field length can vary to transmit any type of information. In one approach, a field can be two bits in length with the first bit indicating a service point and a second bit indicating a control point.

In practice, after a physical device (e.g., ECG wireless sensor) is powered on, a point ID number is autonomously assigned to the device when introduced to a wireless ad hoc network. The assigned point ID number is compared against all other point IDs from other physical devices on the network. If there is a conflict, a new point ID is assigned to the newly introduced physical device. If there is no conflict, the originally assigned point ID is utilized.

FIG. 5 illustrates four multicast addresses 90, 100, 110, 120 wherein a plurality of entities can be addressed at substantially the same time. Each of the multicast addresses 90, 100, 110, 120 provides at least one field 92, 94, 96, 98, 104, 106, 108, 116, 118, 128 that can be utilized with a multicast. In one mode 90, all four fields 92-98 of multicast address 90 are employed. In another mode 120, the point ID field 128 is employed to multicast information to all points on a given patient with a given service type and point type. For example, all pulse sensors on the patient are sensed. In another example 100, all points that relate to one patient are read and/or written to at one time. In another mode 110, all addresses of a given service type on a given patient are addressed. For example, all points of the patient that generate or receive data relating to blood oxygen are addressed. Analogously, other point groups can be addressed: single service points, single control points, all points, all points belonging to the same patient, all points with the same service type regardless of patient, all service points providing the same service type, and/or all control points of a patient consuming the same service type. Based on this addressing schema, a suite of protocols is provided that enables auto addressing of points, discovery and description of service points, control and eventing within a system. As another example, different sensors may use batteries at different rates and have different maintenance schedules. A multi-cast to all ECG sensors can be used to check for low battery responses.

The addressing schema described herein provides several advantages over conventional addressing schemas. The subject addressing schema is more efficient, employing fewer levels of naming indirections with no name resolution required. Addresses are independent of topological location and based on capabilities that are relevant to applications. Assignment of addresses to service and/or control points is simplified by employing automatic autonomous addressing techniques described herein. Address collisions are only possible between points of the same patient and with the same point type and service type. Simple and efficient service discovery and eventing protocols are enabled. The points are self-describing and the multicast groups are built in. In this manner, applications do not have to define and join multicast groups. Instead, messages can be sent to particular locations throughout a network utilizing specific control and/or service point addresses without performing a prior service discovery.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A wireless body network for monitoring a patient, the wireless body network comprising:
   at least one wireless unit coupled to the patient configured to collect and transmit data to the wireless body network related to one physiological function of the patient, the wireless unit employing an addressing scheme, including:
      at least one of a service type field that identifies a service and a point type field that identifies whether the service is provided or consumed;
      a patient identification field that contains a patient identification number that is unique to the wireless body network;
      a point identification field that distinguishes one wireless unit from another when the patient identification field, the service type field and the point type field are identical; and
   a physical device configured to communicate with the wireless unit utilizing the addressing scheme.

2. The system according to claim 1, wherein the at least one wireless unit includes:
   a patient identification module coupled to the patient configured to transmit the unique patient identification number to the wireless body network;
   a physical device which is one of a data processing component, a display device, a data storage unit and a data transmission component.

3. The system according to claim 1, wherein the addressing scheme further includes:
both the service type field to indicate the service and the point type field to indicate whether the wireless unit provides the service or consumes the service.

4. The system of claim 3, wherein at least one of the patient identification field, the service type field, the point type field and the point identification field are designatable as multicast address fields.

5. The system according to claim 3, wherein wireless unit includes both a service point and a control point.

6. The system according to claim 1, wherein the point identification value is autonomously assigned to the wireless unit.

7. The system according to claim 5, wherein the autonomously assigned point identification value is modified by the wireless body network if its address is not unique to avoid a conflict with another physical device.

8. The system according to claim 1, wherein the service type of the wireless unit is one of an electrocardiograph (ECG) sensor, a pulse oximetry (SpO2) sensor, a non-invasive blood pressure (NIBP) sensor, and a temperature sensor.

9. The system according to claim 1, wherein the point type field identifies one of:
a service point which provides a service to the wireless body network and;
a control point which consumes a service provided by another service point.

10. The system according to claim 1, wherein the addressing scheme further includes:
a location field that designates a particular location of one of the physical device and the patient.

11. A method for communicating within a wireless medical sensor network, the method including a plurality of wireless units, comprising:
broadcasting to at least one of the wireless units employing an addressing scheme including:
a patient identification field that contains a patient identification number that is unique to the wireless body network; and
at least one of a service type field that identifies a service and a point type field that identifies whether the service is provided or consumed;
a point identification field that contains the point identification value to distinguish one wireless unit from a disparate wireless unit when the patient identification field, the service type field and the point type field are identical.

12. The method of claim 11, the addressing scheme further including:
both the service type field to identify the service type value and the point type field that contains the point value to indicate whether the wireless unit provides a service or consumes a service.

13. The method according to claim 11, further including:
coupling one of the wireless units to a patient to monitor and transmit information related to a characteristic of the patient to the smart wireless sensor network.

14. The method according to claim 13, further including:
coupling a patient identification module to the patient, the patient identification module having a unique patient identification number in the patient identification field to the smart wireless sensor network.

15. The method according to claim 13, further including:
after coupling the wireless unit to the patient, polling other network devices to determine if its address is unique;
if the coupled wireless unit address is not unique, selecting another assigned point identification value.

16. The method according to claim 13, wherein monitoring a characteristic of the patient includes monitoring at least one of an electrocardiograph (ECG) value, a pulse oximetry (SpO2) value, a non-invasive blood pressure (NIBP) value, and a temperature value.

17. The method according to claim 11, wherein the point type field contains one of a service point which provides a service to the wireless body network and a control point which consumes a service provided by the service point.

18. The method according to claim 11, wherein the addressing scheme further includes:
a location field that designates a particular location related to one of the wireless unit and the patient.

19. The method according to claim 11, further including designating at least one of the patient identification field, the service type field, the point type field and the point identification field as a multicast address field.

20. The method according to claim 11, further including multicasting addressing one of:
all units with a common service point,
all units with a common control point,
all units belonging to a selected patient,
all units of a selected patient providing the same service type,
all units belonging to a selected patient consuming the same service type,
all units.

21. An addressing scheme for a wireless sensor network, comprising:
a patient identification field that contains a patient identification number that is unique to the wireless body network;
at least one of a service type field that contains the service type value that indicates a type of service and a point type field that contains the point value that indicates whether the wireless unit provides the service or consumes the service; and
a point identification field that contains the point identification value to distinguish one wireless unit from a disparate wireless unit when the patient identification field, the service type field and the point type field are identical.

* * * * *